United States Patent [19]

Uemura et al.

[11] Patent Number: 4,898,937
[45] Date of Patent: Feb. 6, 1990

[54] α-CRYSTALS OF CEFAZOLIN SODIUM

[75] Inventors: Toshinobu Uemura, Kishiwada; Keiji Kai, Osaka; Masateru Kodani, Ikeda; Fumiyo Yoshida, Osaka; Matsuhiko Aratani, Daito, all of Japan

[73] Assignee: Fujisawa Pharmaceutical Co., Ltd., Osaka, Japan

[21] Appl. No.: 305,167

[22] Filed: Feb. 2, 1989

[30] Foreign Application Priority Data

Feb. 5, 1988 [JP] Japan .................................. 63-26337

[51] Int. Cl.$^4$ .................. C07D 501/56; A61K 31/545
[52] U.S. Cl. .................................................... 540/227
[58] Field of Search ................. 540/227; 514/192, 195

[56] References Cited

U.S. PATENT DOCUMENTS 4,692,519  9/1987  Maito et al. .......................... 540/227

OTHER PUBLICATIONS

The Merck Index, p. 264, tenth edition (1983).

Primary Examiner—Nicholas S. Rizzo
Attorney, Agent, or Firm—Oblon, Spivak, McClelland, Maier & Neustadt

[57] ABSTRACT

This invention relates to α-crystals of cefazolin sodium with a water content in the range of 13.0 to 15.8%, useful as an antibiotic of improved thermal and light stability.

2 Claims, No Drawings

α-CRYSTALS OF CEFAZOLIN SODIUM

This invention relates to α-crystals of cefazolin sodium of the formula

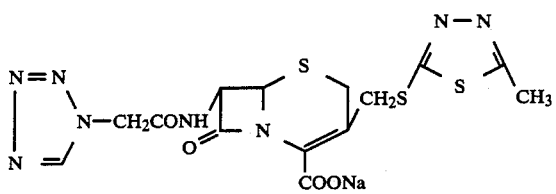

and is of use in the field of health care.

Cefazolin sodium is a broard-spectrum antibiotic which has been employed widely as reconstitutable parenteral products just prior to use. In such parenteral products commercially available these days, either a lyophilizate of β-crystals, i.e. 3/2 hydrate, are generally used.

Aside from these forms, cefazolin sodium is known to exist in the form of α-crystals, i.e. pentahydrate (theoretical water content 15.9%). It is known that the α-crystals are superior to said lyophilizate and β-crystals in stability to light. In regard to thermal stability, however, the α-crystals are significantly inferior to said other forms at elevated temperatures not less than 40° C., although the former crystals are more stable at room temperature. It is for this reason that the α-crystals have not been developed commercially to this day.

The inventors of this invention conducted an intensive and diligent research to improve the high-temperature stability of α-crystals of cefazolin which are more stable to light than said lyophilizate and β-crystals. As a result, it was found that a portion of the 5 molecules of water contained in the α-crystal is so labile that it is ready to leave off at an elevated temperature of 40° C. or more, and that this labile water induces a transformation from α-crystal to β-crystal (theoretical water content 5.4%) which, in turn, sets off a massive release of water to make the whole crystal unstable. It was further found that if this labile water is removed to provide an α-crystal with a water content of 13.0 to 15.8%, the above transformation to β-crystal is inhibited and that this α-crystal is remarkably superior to the usual α-crystal (theoretical water content 15.9%) in stability at elevated temperatures not less than 40° C.

It was also verified that this α-crystal is not less stable than the lyophilizate and β-crystals at elevated temperatures not less than 40° C. and yet fully retains the characteristic stability to light of the usual α-crystals.

The α-crystals of cefazolin sodium having a water content of 13.0 to 15.8% according to this invention can be produced by the following and other procedures.

Thus, in accordance with the Jounral of Antibiotics 23 (3), 135 (1970), cefazolin is dissolved in an aqueous solution of sodium bicarbonate or sodium hydroxide and, then, an organic solvent (for example, ethanol, isopropyl alcohol, acetone or the like or a mixture thereof) is added dropwise to the solution to cause crystallization.

The resulting α-crystals of cefazolin sodium are recovered by filtration and washed with the above-mentioned organic solvent.

Then, drying these α-crystals of cefazolin sodium in vacuo gives the desired α-crystals of cefazolin sodium with a water content of 13.0 to 15.8%.

While the degree of vacuum, shelf temperature and time settings for vacuum drying can be appropriately chosen according to the desired water content of α-crystals, typical sets of conditions are shown in the examples which appear hereinafter.

As an alternative, instead of drying the usual α-crystals of cefazolin sodium in vacuo, the following procedure may be followed to give the desired α-crystals of cefazolin sodium with a water content of 13.0–15.8%. Thus, α-crystals of cefazolin sodium with a water content of 15.9% are first prepared by drying in the air or in a current of air and these α-crystals are then kept in a desiccator containing a salt of an organic or inorganic acid (for example, potassium carbonate, magnesium chloride, lithium chloride, etc.) and, as such, having a controlled relative humidity at room temperature for about 1 to 3 days.

The above-mentioned organic or inorganic acid salt to be used for controlling the relative humidity can be selected according to the desired water content of product α-crystals and typical species are mentioned in the examples which appear hereinafter.

The resulting α-crystals of cefazolin sodium with a water content of 13.0 to 15.8% are generally filled into vials and put to use.

It is to be noted that X-ray diffraction analysis revealed that cefazolin sodium having a water content of 13.0 to 15.8% gives the same diffraction pattern as the usual α-crystals of cefazolin sodium with a water content of 15.9% and is, therefore, alpha in crystal form. It was also found that when the water content of cefazolin sodium crystals is decreased to less than about 14.5%, the α-crystals begin to be contaminated with amorphous form, that the production of this amorphous phase increases with decreasing water content and that the larger the proportion of amorphous phase, the less stable is the product. Therefore, the preferred range of water content for the α-crystals of cefazolin sodium of this invention is 14.5 to 15.8%. It was further found that when the water content is decreased to less than 13.0%, the stability to light is sacrificed.

The characteristics of α-crystals of cefazolin sodium of this invention can be appreciated from the following test examples.

THERMAL STABILITY TEST 1

Method

The α-crystals of cefazolin sodium (1 g potency) with varying water contents as obtained in Example 1, Examples 2-(a) through 2-(d) and Reference Examples 1 and 2 were respectively filled into vials and sealed. The capped vials were stored in an incubator at 50° C. and the time-course changes of appearance were monitored.

Results

The test results are shown below in the table.

| Sample | Water content (%) | Time in days to onset of change in appearance (melting and coloration) |
| --- | --- | --- |
| Reference Example 2 | 16.1 | 14 |
| Reference Example 1 | 15.9 | 14 |
| Example 2-(a) | 15.8 | 155 |
| Example 1 | 15.4 | No change in appearance |

-continued

| Sample | Water content (%) | Time in days to onset of change in appearance (melting and coloration) |
|---|---|---|
| | | after 155 days |
| Example 2-(b) | 14.4 | Same as Example 1 |
| Example 2-(c) | 13.4 | Same as Example 1 |
| Example 2-(d) | 13.0 | Same as Example 1 |

It is apparent from the above results that the α-crystals of cefazolin sodium (water contents 13.0–15.8%) of this invention as obtained in Examples 1 and 2-(a) through 2-(d) are by far superior to the usual α-crystals (water content 15.9%) obtained in Reference Example 1 and the water-rich α-crystals (water content 16.1%) obtained in Reference Example 2 in terms of stability at 50° C.

THERMAL STABILITY TEST 2

Method

The samples (1 g potency) prepared in Examples 1 and 4 and Reference Example 1, which appear hereinafter, were respectively filled into vials and sealed.

At the same time, the corresponding samples were respectively dissolved in distilled water and the color [transmittance at 400 nm; hereinafter referred to as T 400%], pH and potency (assayed by liquid chromatography) of each sample were determined as initial values.

The samples in vials were respectively stored in an incubator at 40° C. for 6 months.

As a control, a commercial cefazolin sodium preparation (manufactured by Fujisawa Pharmaceutical Co., Ltd., 1 g potency, lyophilizate) was concurrently stored.

After 6 months, each sample was reconstituted with distilled water and its color, pH and potency were determined in the same manner as initial samples.

Results

The test results are shwon below in the table.

| Storage conditions | | 40° C. | |
|---|---|---|---|
| Sample | Parameters | Initial | 6 Months |
| Reference Example 1 | Color T400% | 88.9 | 32.8 |
| (water content 15.9%) | pH | 5.65 | 6.10 |
| | Residual potency (%) | 100 | 95.1 |
| Example 1 | Color T400% | 90.4 | 82.6 |
| (water content 15.4%) | pH | 5.72 | 5.63 |
| | Residual potency (%) | 100 | 99.0 |
| Example 4 | Color T400% | 88.0 | 82.4 |
| (water content 15.1%) | pH | 5.65 | 5.56 |
| | Residual potency (%) | 100 | 99.3 |
| Lyophilizate | Color T400% | 77.7 | 56.7 |
| | pH | 5.13 | 4.99 |
| | Residual potency (%) | 100 | 99.0 |

It is apparent from the above results that the α-crystals of this invention as prepared in Examples 1 and 4 are by far superior to the α-crystals of Reference Example 1 in terms of stability at 40° C. It is also seen that the stability of these α-crystals of this invention is comparable or even superior to that of the commercial lyophilizate.

LIGHT STABILITY TEST 1

Method

The sample (1 g potency) obtained in Example 5 which appears hereinafter was filled into a vial and sealed. The capped vial was then stored under fluorescent light (luminous intensity: 500 lux) for 3 months. The sample was then reconstituted with distilled water and its color T400%, pH and potency were determined in the same manner as in thermal stability test 2 and compared with the initial values.

Results

| Storage conditions | | Under fluorescent light (500 lux) | |
|---|---|---|---|
| Sample | Parameter | Initial | 3 Months |
| Example 5 | Color T400% | 90.6 | 89.0 |
| (water content 15.5%) | pH | 5.72 | 5.60 |
| | Residual potency (%) | 100 | 99.6 |

It is apparent from the above results that the α-crystals of this invention fully retain the inherent stability to light.

LIGHT STABILITY TEST 2

Method

The samples (1 g potency) obtained in Examples and Reference Examples, which appear hereinafter, were filled into vials and sealed. The capped vials were then stored in an artificial light chamber (luminous intensity: 20,000 lux, temperature: 25° C.) for 5 days. Each sample was then reconstituted with distilled water and its color T400% was determined in the same manner as in thermal stability test 2 and compared with the initial value.

Results

The test results are shown below in the table.

| Storage conditions | | Artificial light chamber (20,000 lux 25° C.) | |
|---|---|---|---|
| Sample | Parameter | Initial | 5 days |
| Reference Example 1 (water content 15.9%) | Color T400% | 88.9 | 87.1 |
| Example 2-(a) (water content 15.8%) | Color T400% | 84.0 | 80.9 |
| Example 3 (water content 14.5%) | Color T400% | 84.8 | 79.1 |
| Reference Example 3 (water content 10.8%) | Color T400% | 85.2 | 55.0 |

It is apparent from the above results that the α-crystals of this invention, especially the α-crystals with a water content in the range of 14.5 to 15.8%, are stable to light as well as the usual α-crystals (water content 15.9%).

Further it is found that the α-crystals with a low water content are unstable to light.

REFERENCE EXAMPLE 1

α-Crystals of cefazolin sodium with a water content of 15.9% were prepared by the method described in the Journal of Antibiotics 23 (3), 135 (1970).

REFERENCE EXAMPLE 2

The α-crystals of cefazolin sodium with a water content of 15.9% as prepared in Reference Example 1 were stored in a desiccator with a relative humidity of 75% (controlled with a saturated aqueous solution of sodium chloride) at room temperature for 1 day to provide α-crystals of cefazolin sodium with a water content of 16.1%.

REFERENCE EXAMPLE 3

The α-crystals obtained in the same manner as Example 3-(i), which appear hereinafter, were dried in vacuo (drying conditions: 10 mmHg, shelf temperature 35° C., 2 hours) to give α-crystals of cefazolin sodium with a water content of 10.8%.

[EXAMPLES]

The following examples are intended to illustrate this invention in further detail.

EXAMPLE 1

The α-crystals of cefazolin sodium with a water content of 15.9% as prepared in Reference Example 1 were stored in a desiccator with a relative humidity of 42.8% (controlled with a saturated aqueous solution of potassium carbonate) at room temperature for 1 day to provide α-crystals of cefazolin sodium with a water content of 15.4%.

EXAMPLE 2

In the same manner as Example 1, the α-crystals of cefazolin sodium with a water content of 15.9% as prepared in Reference Example 1 were stored in desiccators with varying relative humidities at room temperature for 1 to 3 days to provide α-crystals of cefazolin sodium with the under-mentioned water contents.

(a) The same starting material α-crystals were stored at a relative humidity of 52.8% (controlled with a saturated aqueous solution of magnesium nitrate) for 1 day to give α-crystals of cefazolin sodium with a water content of 15.8%.

(b) The starting material α-crystals were stored at a relative humidity of 11% (controlled with a saturated aqueous solution of lithium chloride) for 1 day to give α-crystals of cefazolin sodium with a water content of 14.4%.

(c) The starting material α-crystals were stored at a relative humidity of 11% for 2 day to give α-crystals of cefazolin sodium with a water content of 13.4%.

(d) The starting material α-crystals were stored at a relative humidity of 11% for 3 days to give α-crystals of cefazolin sodium with a water content of 13.0%.

EXAMPLE 3

(i) To cefazolin (100 g potency) were added sodium bicarbonate (18.5 g) and distilled water (193.6 ml) at 30° C. to prepare an aqueous solution of cefazolin sodium. At the same temperature, 99% ethanol (968 ml) was added dropwise to the solution for 60 minutes to precipitate α-crystals of cefazolin sodium, followed by cooling with ice. The precipitate was recovered by filtration through a glass filter and washed with 99% ethanol (150 ml) to recover α-crystals of cefazolin sodium.

(ii) The above α-crystals were dried in vacuo (20 mmHg, shelf temperature 35° C.) for 5 hours to give α-crystals of cefazolin sodium with a water content of 14.5% (114.3 g).

EXAMPLE 4

The α-crystals obtained in the same manner as Example 3-(i) were dried in vacuo (drying conditions: 20 mmHg, shelf temperature 35° C., 3 hours) to give α-crystals of cefazolin sodium with a water content of 15.1%.

EXAMPLE 5

The α-crystals obtained in the same manner as Example 3-(i) were dried in vacuo (drying conditions: 20 mmHg, shelf temperature 35° C., 2 hours) to give α-crystals of cefazolin sodium with a water content of 15.5%.

EXAMPLE 6

The α-crystals (100 g) obtained in Example 3-(i) were dried in the air and, then, stored in a desiccator with a relative humidity of 32.8% (controlled with a saturated aqueous solution of magnesium chloride) at room temperature for 1 day to give α-crystals of cefazolin sodium with a water content of 15.2%.

What is claimed is:

1. α-Crystals of cefazolin sodium with a water content in the range of 13.0 to 15.8 percent.

2. α-Crystals of cefazolin sodium according to claim 1, wherein the water content is in the range of 14.5 to 15.8 percent.

* * * * *